(12) United States Patent
Davis

(10) Patent No.: US 7,101,346 B1
(45) Date of Patent: Sep. 5, 2006

(54) DYNAMIC RESPONSE ANKLE-FOOT ORTHOSIS WITH JOINT

(76) Inventor: Locke Davis, 6 Oliver Ct., Signal Mountain, TN (US) 37377

( * ) Notice: Subject to any disclaimer, the term of this patent is extended or adjusted under 35 U.S.C. 154(b) by 365 days.

(21) Appl. No.: 10/308,678

(22) Filed: Dec. 3, 2002

Related U.S. Application Data

(60) Continuation-in-part of application No. 09/878,621, filed on Jun. 11, 2001, now Pat. No. 6,726,645, which is a division of application No. 09/405,074, filed on Sep. 27, 1999, now Pat. No. 6,334,854.

(51) Int. Cl.
*A61F 5/00* (2006.01)

(52) U.S. Cl. .................. 602/5; 602/23; 602/27

(58) Field of Classification Search .......... 602/5–8, 602/20, 23, 26–27; 482/34.9
See application file for complete search history.

(56) References Cited

U.S. PATENT DOCUMENTS

| 5,573,501 A | * | 11/1996 | Ruscito et al. | 602/7 |
| 5,759,168 A | * | 6/1998 | Bussell et al. | 602/27 |
| 6,146,344 A | * | 11/2000 | Bader | 602/6 |

* cited by examiner

*Primary Examiner*—Michael A. Brown
(74) *Attorney, Agent, or Firm*—Stephen J. Stark; Miller & Martin PLLC

(57) ABSTRACT

An orthotic device is developed and customized to control the (un)desired movements of the patient's defective lower limb. The device incorporates a footplate made of a rubber like elastomeric material, a proximal segment that encompasses the foot at the metatarsal phalengeal joints and the dorsal aspect of the foot, and a second proximal segment that encompasses the shin portion of the leg. Motion of the patient's talocrual is allowed and controlled by laminating mechanical joints to the medial and lateral aspects of the brace and providing cutouts in the lamination just anterior and posterior to the ankle joint axis of motion.

18 Claims, 3 Drawing Sheets

DYNAMIC RESPONSE ANKLE-FOOT ORTHOSIS WITH JOINT

CLAIM OF PRIORITY

This application is a continuation-in-part filed Jun. 11, 2001 of U.S. patent application Ser. No. 09/878,621 now U.S. Pat. No. 6,726,645, which is a divisional application filed Sep. 27, 1999 of U.S. patent application Ser. No. 09/405,074 now U.S. Pat. No. 6,334,854.

BACKGROUND OF THE INVENTION

1. Field of the Invention

This application relates to orthoses, and more particularly to ankle-foot orthotic braces which have a joint for allowing movement along a rotational axis.

2. Detailed Description of Related Art

Ankle foot orthoses are commonly used as foot, ankle, and leg braces for improving movement. Years ago a leg brace would consist of two metal bars and a stirrup attached to the sole of the shoe. A horizontally positioned padded, metal band, contoured to the back of the leg calf, would connect the two metal bars. A broad strap across the anterior section of the calf would hold the brace in place. This type of brace has limited use today, but is not considered to be state of the art orthotic management. This type of device lacks biomechanical control of the foot and ankle and is cumbersome and heavy. It would be very difficult to adapt this brace to athletic applications since the metal bars would pose a hazard for the user, and possibly to other participants in the sport.

A modern ankle foot orthosis, being a device that applies biomechanical forces to a body segment, is usually fabricated from thermoplastics. The thermoplastic is heat molded over a positive mold similar in shape to the patient's limb, then cooled, and trimmed. Often the thermoplastic is formed into rigid laminates of non-resilient material. Ankle joint motion in the orthotic device is often provided by a mechanical hinge type joint at the ankle joint. Once again, these devices may pose a hazard to the user and others, especially when used in contact sports.

An existing fundamental problem of orthotic management is that a rigid orthosis, which does not allow plantar flexion of the ankle, will also prevent extension of the hip and knee and causes instability in the hip and knee. Balance at the foot-ankle complex cannot properly develop because activity and sensation of movement is limited, with resultant muscle wasting. These rigid orthosis are sometimes utilized for rehabilitating athletes, but provide a potential for possibly injuring the user or other participants in a sport.

Current orthotic technology does not allow triplanar activity of the foot and ankle in stance phase found in normal gait. The use of very thin or more flexible plastics has been attempted to allow more motion in the foot and ankle. Much of the benefit of wearing an orthosis is lost when using very flexible, but still non-deformable and non-resilient, plastics, however, in cases where significant control is needed for spastic muscle activity, pathomechanical deformities, or athletic activities following an injury or other problem. The very flexible plastics reduce stability to allow mobility. Allowing motion is not the same as promoting and controlling more normal motion. The disclosure of the present invention promotes and controls more normal motion.

For many patients who require the use of an ankle-foot orthosis, current orthotic technology does not adequately address the dynamic changes that occur in the foot and ankle complex during the gait cycle. Triplanar motion of the foot and ankle requires a dynamic response. Current technology either positions the segments of the foot in a static position or allows motions to occur by reducing the corrective forces. The use of a mechanical ankle joint with a rigid frame may provide motion of the talocrural joint in the sagittal plane, however complex motions required within the foot, are restricted from a normal biomechanical response because of the static forces applied by the brace. Optimal orthotic management should control abnormal motion by restricting specific motion during specific events of the gait cycle. This cannot be achieved by holding the segments of the foot in an uniform position throughout the gait cycle. The foot must remain a mobile entity that engages in the normal activity of gait, but is prevented from abnormal motion. Because the needs of the corrective forces of the foot and ankle complex differ within different events of the gait cycle, a need exists for an orthosis which is dynamic in its application of corrective forces.

SUMMARY OF THE INVENTION

Through a dynamic orthosis, a more normal gait pattern can be obtained with less compensatory activity required by proximal segments of the body. The present invention, with its pliable dynamically responding ankle-foot orthosis, provides predetermined corrective forces on the foot and ankle complex during different events of the gait cycle. By combining a dynamically responsive orthosis with a pivot location, such as a mechanical joint, the orthosis, which began as a treatment for gait impaired individuals, has now become an attractive option for athletic applications. The orthosis may be constructed to be flexible so that when impacted, the individual wearing the orthosis is preferably not subjected to a rigid collision by the orthosis. Other applications may also exist where the patient requires freer motion of the talocrual joint, but a limited range of motion of the subtalar joint and positioning segments of the distal segments of the foot.

An example of a possible user would be a patient who has a great deal of medial lateral instability of the subtalar joint, but is able to control plantar flexation and dorsiflexion of the talocrual joint. This type of scenario is common in athletes who have good mobility and control of the ankle foot complex, but experience lateral ligament weakness or posterior tibialis weakness during high exertion. In order for this patient to compete effectively in the athletic arena, they must have a full range of motion of the talocrual joint, but be protected from inverting or everting beyond the normal physiologic range during athletic competition. The orthosis shown and described herein provides an intimate fit and control of a dynamic response orthosis, while allowing increased mobility of the talocrual joint during ambulation and high impact activities such as running and playing sports which require quick moves to the left or right.

The purpose of this invention is to provide an improved method of controlling the movement of a patient's defective lower limb. The method and device provides an improved system of constructing a customized ankle-foot orthosis. A combination of physical therapy assessment and orthotic evaluation is utilized to determine design characteristics of the orthosis needed for controlling and improving movement of the defective lower limb movement.

Various other features of the method of the present invention will become obvious to those skilled in the art upon reading the disclosure

BRIEF DESCRIPTION OF DRAWINGS

The particular features and advantages of the invention as well as other objects will become apparent from the following description taken in connection with the accompanying drawings in which.

DETAILED DESCRIPTION OF THE DRAWINGS

Figure 1:
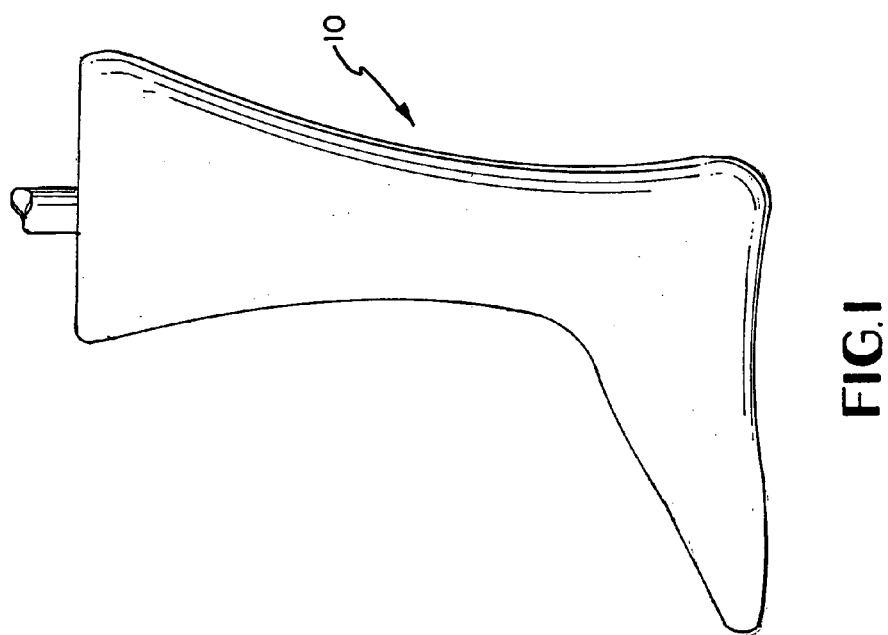
FIG. 1 is a side plan view of the a positive mold made of a lower limb of a patient.

Referring now to FIG. 1, a positive mold 10 of the foot of a patient is illustrated. U.S. Pat. No. 6,334,854 incorporated herein by reference describes one method of making mold 10. A cast is typically taken of a patient's leg and foot. The cast is then sealed and poured with molding plaster. After the molding plaster has hardened, the outer cast is removed and the technician is left with a positive mold of the patient's lower limb. This positive mold 10 may then be modified and smoothed according to specifications desired by the clinician. Additionally, molds 10 can be created according to the measurements taken from the limb of a patient to create mold 10.

Figure 2:
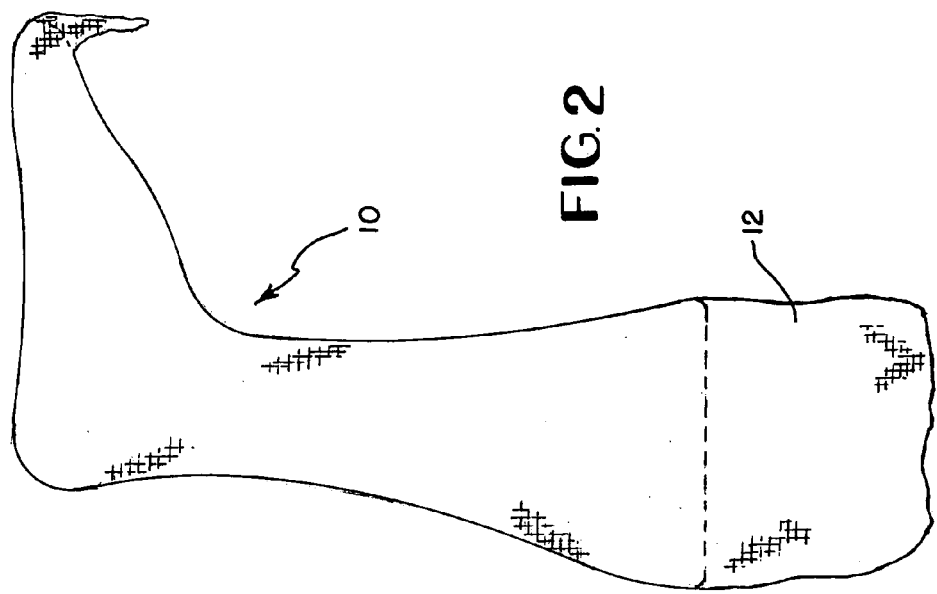
FIG. 2 is a side plan view of the mold of FIG. 1 with a fabric placed thereabout.

After obtaining a suitable mold 10, the mold is sealed with a sealing and release agent that will seal the mold and not bond to the elastomeric resin. FIG. 2 shows a fabric 12 placed over the mold 10. The fabric 12 may be a nylon stockinette or other appropriate material such as one having a high tensile strength material fabric has been found to provide a suitable fabric layer 12. Next, the reinforcement portions 14 such as DACRON™, felt or other appropriate materials can be positioned around the heel area 16 as shown, or other appropriate locations, to provide increased strength and thickness or for other purposes, such as those described in U.S. Pat. No. 6,334,854. Joints 18,19 are then placed at the desired location on either side of where the ankle will bend. The joint 18 is illustrated as an articulating ankle joint segment which is adhered to the fabric 12 with a spray adhesive or other appropriate connector so that the joint 18 does not move during the remaining portions of the fabrication process. Additional layers of fabric 12 may then be placed over the joint 18 and reinforcement portion 16 to sandwich the joints 18,19 between fabric layers.

Figure 4:
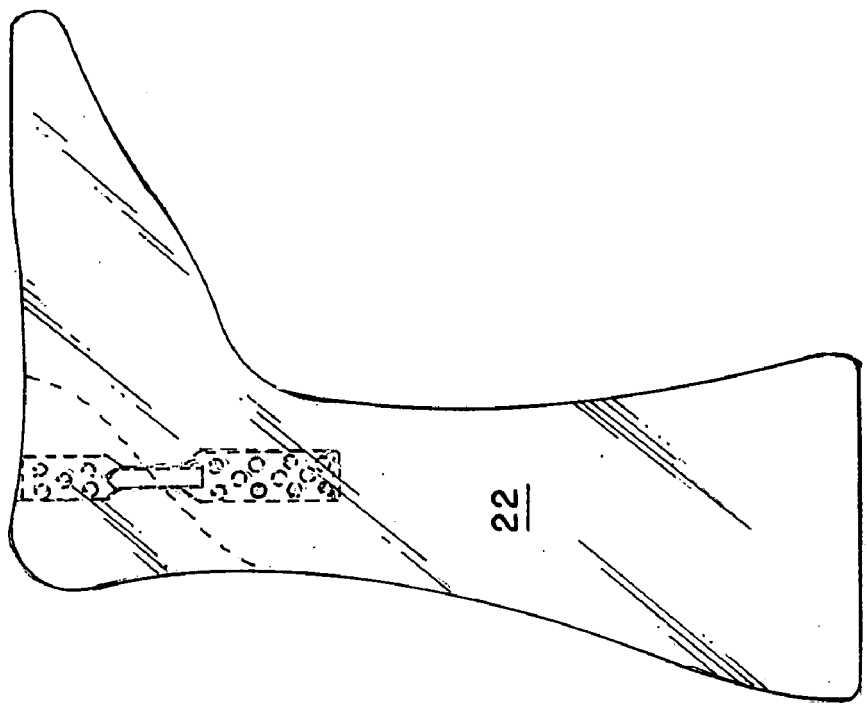
FIG. 4 is a side plan view of the mold of FIG. 3 with elastomeric resin coating and the fabric layer.
Figure 3:
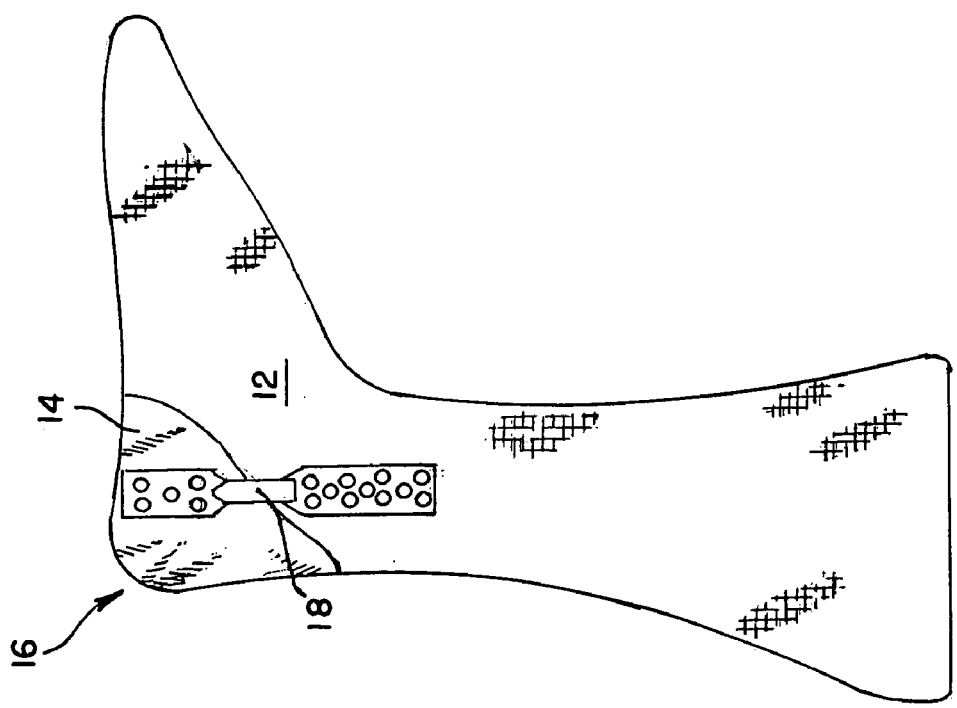
FIG. 3 is a side plan view of the mold with the fabric of FIG. 2 with reinforcements and a joint placed thereon and a second fabric layer placed thereon.

Liquid elastomeric resin is then applied, preferably substantially described in U.S. Pat. No. 6,334,854 so that the elastomeric liquid is introduced to the fabric 12 which fully allows the saturation of the elastomeric liquid into the multiple layers of fabric 12. The elastomeric material is believed to saturate into the fabric 12 to create a lamination between and about the multiple layers of fabric 12 as well as encapsulating the mechanical ankle joint 18. The elastomeric liquid cures preferably under a vacuum to form elastomeric layer 22 shown in FIG. 4 which covers the joint 18 and heel reinforcement 14.

Figure 5:
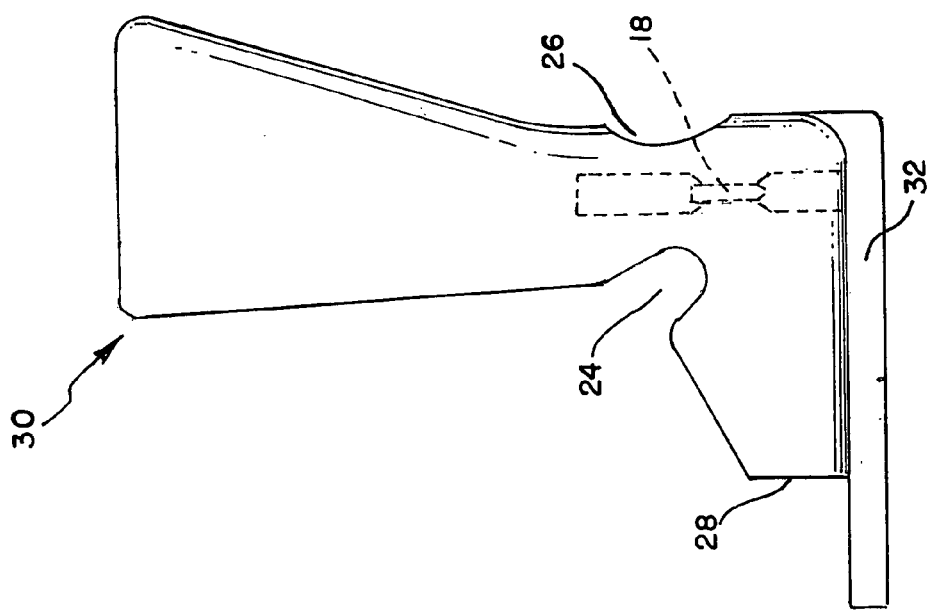
FIG. 5 is a side plan view the orthosis of FIG. 4 with portions cutaway to allow for greater mobility.

In FIG. 5, cutouts 24,26 are made preferably on either side of the joints 18 (obscured from view on the other side of the ankle). Additionally, toe cutout 28 may also be made as well. Furthermore, the lay up 30 may be sliced so that it may enable a user to more easily place the lay up 30 about the user's leg as an orthosis. A foot pad 32 may be connected at the bottom of the lay up 30 as described in U.S. Pat. No. 6,324,854 or otherwise.

Figure 6:
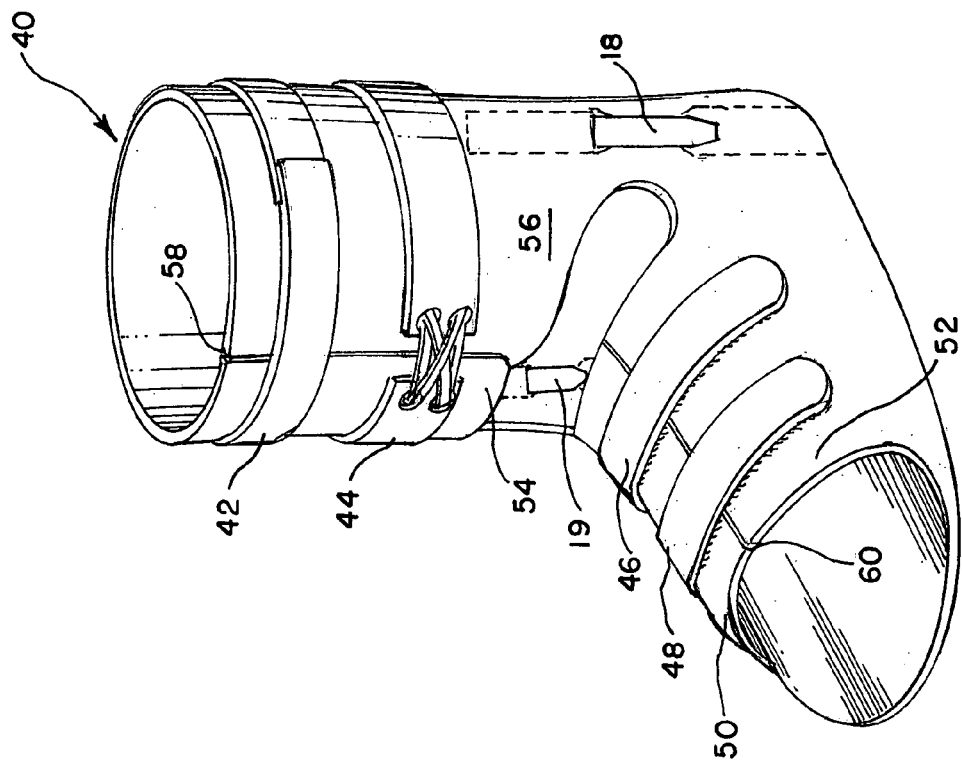
FIG. 6 is a front elevational view of the orthosis of FIG. 5.

FIG. 6 shows a completed orthosis 40 ready for use by a user. Joints 18,19 are preferably located opposite the ankle of a user when installed. Cutouts 24,26 assist a user in being able to bend the ankle for movement along a single axis rotation. The remainder of the orthosis 40 is believed to restrain movement so as to protect ligaments or other portions of the leg from abnormal and unwanted motion of the foot and leg without requiring a rigid substrate.

When the completed orthosis 40 is fabricated as shown in FIG. 6, the orthosis 40 includes a matrix of fabric 12 which is impregnated with elastomeric resin 22 which forms a layer which encapsulates, or substantially encapsulates, and covers the fabric 12. It is further proposed that there be multiple layers of fabric with reinforcements 14 therebetween as well as joints 18,19 located therebetween to allow an axis of rotation which corresponds with a natural rotating axis of a joint such as the ankle as illustrated. Cutouts in the orthosis 40 are specifically provided to assist in providing a range of motion by the user.

Straps 42,44,46,48 shown in FIG. 6 to connect portions 50,52 and 54,56 respectively which are separated by slits 58,60. The straps 42,44,46,48 may be connected by hook and loop fasteners or otherwise. The straps 42,44,46,48 are also believed to add additional strength to the orthosis 40. In FIG. 6, both joints 18,19 are illustrated and it is evident that the orthosis 40 is bendable about the joints 18,19 for use in athletics or otherwise.

Numerous alterations of the structure herein disclosed will suggest themselves to those skilled in the art. However, it is to be understood that the present disclosure relates to the preferred embodiment of the invention which is for purposes of illustration only and not to be construed as a limitation of the invention. All such modifications which do not depart from the spirit of the invention are intended to be included within the scope of the appended claims.

Having thus set forth the nature of the invention, what is claimed herein is:

1. An ankle foot orthosis for use with an ankle and foot of a patient, said orthosis comprising:
   a laminated set-up having
   a) at least one first fabric layer;
   b) at least one second fabric layer
   c) a laminate of elastomeric resin in the at least one first and second fabric layers;
   wherein said laminated set up forms a matrix which substantially surrounds a portion of the foot and the ankle of the patient;
   and a joint located relative to the ankle which assists in allowing a predetermined range of ankle motion with at least a portion of the joint located intermediate the first and second fabric layers.

2. The ankle foot orthosis of claim 1 wherein the at least one first fabric layer is comprised of a stockinette material.

3. The ankle foot orthosis of claim 2 wherein the joint further comprises opposing joints which allow rotation about a talocrual joint of a user.

4. The ankle foot orthosis of claim 1 wherein the at least one second fabric layer is comprised of a stockinette material.

5. The ankle foot orthosis of claim 1 further comprising at least one of an arch support and a foot support located below a plantar section of the foot.

6. The ankle foot orthosis of claim 5 wherein the at least one of the arch support and the foot support is comprised of an elastomeric material.

7. The ankle foot orthosis of claim 1 further comprising a placket, wherein said placket allows
the orthosis to be positioned about the ankle and foot of the patient.

8. The ankle foot orthosis of claim 7 further comprising closing means to substantially close said placket for the orthosis to substantially surround said ankle and foot portion of said patient.

9. The ankle foot orthosis of claim 1 further comprising a reinforcement portion laminated into the matrix further comprising a cutout proximate to the at least one joint which assists in allowing rotational motion about the at least joint.

10. An ankle foot orthosis for use with an ankle and foot of a patient, said orthosis comprising:
   a laminated set-up having
   a) at least one first fabric layer;
   b) a reinforcement over the at least one fabric layer; and
   c) an elastomeric resin laminated into the at least one fabric layer and over at least the reinforcement;
   wherein said laminated set up substantially encloses a portion of the foot and the ankle of the patient; and
   opposing joints connected to the laminated set up with at least portions of the joints disposed intermediate the first fabric layer and the reinforcement which assist in allowing a predetermined lower limb movement.

11. The ankle foot orthosis of claim 10 further comprising cutouts in front and behind the joints.

12. The ankle foot orthosis of claim 11 further comprising a second fabric layer over the first fabric layer and joints which is laminated with the elastomeric laminate.

13. An orthosis comprising a laminated set up having at least one first fabric layer, and an elastomeric resin laminate into the at least one fabric layer, wherein said laminated set up substantially encloses a portion of the foot and the ankle of the patient, said laminated set up formed by the process comprising:
   a) creating a mold of a lower leg of patient;
   b) establishing the at least one first fabric layer over a portion of the mold;
   c) placing a joint at an ankle location with at least a portion of the joint over the at least one first fabric layers
   d) placing said at least one second fabric layer over said at least one first fabric layer and the at least a portion of the joint;
   e) establishing an elastomeric laminate through the at least one second fabric layer into the at least one first fabric layer to complete the laminated set up; and
   f) removing the laminated set up from mold for use on a lower limb of a patient.

14. The laminated set up of claim 13 wherein the step of removing of the laminated set up further comprises providing a placket along a portion of the set up, wherein said placket allows for the set up to be placed about the lower limb of the patient and said placket is adapted to close to substantially surround the lower limb.

15. The laminated set up of claim 14 wherein the placket extends along a cut from a top of a shin portion of the set up to a top of a toe portion of the set up.

16. The laminated set up of claim 13 further comprising the step of providing closure means to secure the set up about the lower limb of a patient.

17. The laminated set up of claim 13 further comprising the step of an arch removing material to form a cutout proximate to the joint.

18. The laminated set up of claim 13 further comprising the step of laminating the joint intermediate fabric layers prior to establishing the elastomeric laminate.

* * * * *